United States Patent
Gordinier et al.

(10) Patent No.: US 12,201,717 B2
(45) Date of Patent: Jan. 21, 2025

(54) COMPOSITIONS AND METHODS FOR SUPPORTING SKIN BARRIER HOMEOSTASIS

(71) Applicant: Skinfix Inc., Halifax (CA)

(72) Inventors: Amy Gordinier, Halifax (CA); Marc Cornell, Freehold, NJ (US); Erica Arnoldin, Waverley (CA)

(73) Assignee: Skinfix Inc., Halifax (CA)

( * ) Notice: Subject to any disclaimer, the term of this patent is extended or adjusted under 35 U.S.C. 154(b) by 0 days.

(21) Appl. No.: 18/497,102

(22) Filed: Oct. 30, 2023

(65) Prior Publication Data

US 2024/0139095 A1 May 2, 2024

Related U.S. Application Data

(60) Provisional application No. 63/381,643, filed on Oct. 31, 2022.

(51) Int. Cl.

| | | |
|---|---|---|
| *A61K 8/9789* | (2017.01) | |
| *A61K 8/31* | (2006.01) | |
| *A61K 8/34* | (2006.01) | |
| *A61K 8/365* | (2006.01) | |
| *A61K 8/42* | (2006.01) | |
| *A61K 8/63* | (2006.01) | |
| *A61K 8/64* | (2006.01) | |
| *A61K 8/67* | (2006.01) | |
| *A61K 8/9717* | (2017.01) | |
| *A61Q 19/00* | (2006.01) | |
| *A61Q 19/08* | (2006.01) | |

(52) U.S. Cl.
CPC .............. *A61K 8/9789* (2017.08); *A61K 8/31* (2013.01); *A61K 8/345* (2013.01); *A61K 8/365* (2013.01); *A61K 8/42* (2013.01); *A61K 8/63* (2013.01); *A61K 8/64* (2013.01); *A61K 8/673* (2013.01); *A61K 8/9717* (2017.08); *A61Q 19/007* (2013.01); *A61Q 19/08* (2013.01); *A61K 2800/5922* (2013.01); *A61K 2800/884* (2013.01)

(58) Field of Classification Search
CPC ........ A61K 8/9789; A61K 8/31; A61K 8/345; A61K 8/365; A61K 8/42; A61K 8/63; A61K 8/64; A61K 8/673; A61K 8/9717; A61K 2800/5922; A61K 2800/884; A61Q 19/007; A61Q 19/08

USPC ......................................................... 424/401
See application file for complete search history.

(56) References Cited

U.S. PATENT DOCUMENTS

| | | | |
|---|---|---|---|
| 2008/0206169 A1* | 8/2008 | Millikin | A61K 8/9728 514/263.34 |
| 2011/0217249 A1 | 9/2011 | Dreher | |
| 2014/0105844 A1* | 4/2014 | Brown | A61K 8/361 424/70.1 |
| 2014/0308372 A1 | 10/2014 | Soudant et al. | |
| 2016/0303034 A1* | 10/2016 | Collins | A61K 8/676 |
| 2017/0042784 A1* | 2/2017 | Munk | A61Q 19/00 |
| 2020/0002377 A1 | 1/2020 | Van Den Nest et al. | |
| 2021/0045983 A1 | 2/2021 | Stuhlmann et al. | |
| 2021/0361553 A1* | 11/2021 | Nakhla | A61K 8/735 |
| 2022/0124572 A1 | 4/2022 | Albarano | |

FOREIGN PATENT DOCUMENTS

KR 2021096726 A * 8/2021

OTHER PUBLICATIONS

"Ah, KR 2021096726 A, Aug. 6, 2021, Machine translation" (Year: 2021).*
Watson, "13 Reasons to Add Jojoba Oil to Your Skin Care Routine," Health.com, available at http://www.healthline.com/health/beauty-skin-care/jojoba-oil-for-face (2018).
Williams et al., "Folate in Skin Cancer Prevention," Subcellular Biochemistry, 56: 181-197 (2012).

* cited by examiner

*Primary Examiner* — Isaac Shomer
*Assistant Examiner* — Bryan James Rego
(74) *Attorney, Agent, or Firm* — MEDLER FERRO WOODHOUSE & MILLS PLLC

(57) ABSTRACT

The present disclosure is directed to the use of a composition comprised of: (1) a first active blend of at least: (a) Jojoba oil/Macadamia seed oil esters; (b) squalene; (c) phytosteryl macadamiate; and (d) phytosterols; (2) a second active blend of at least: (e) EGF growth factor; (f) IGF-1 growth factor; (g) acidic FGF growth factor; (h) basic FGF growth factor; (i) VEGF growth factor; (j) vitamin B9; and (k) acetyl glutamine; and (3) a third active blend of at least: (l) an extract of lithothamnium calcareum; (m) pentylene glycol; (n) lactic acid; and (o) glycerin; (4) an emulsifier; and (5) a dermatologically acceptable carrier which, when applied onto skin, helps to positively influence inflammation, hydration, and keratinocyte hyperproliferation, thereby supporting skin barrier health, integrity, and functionality.

12 Claims, No Drawings

COMPOSITIONS AND METHODS FOR SUPPORTING SKIN BARRIER HOMEOSTASIS

CROSS-REFERENCE TO RELATED APPLICATIONS

The present application claims benefit of U.S. Provisional Application No. 63/381,643, filed Oct. 31, 2023, the disclosure of which is incorporated by reference herein in its entirety.

FIELD OF THE INVENTION

The present disclosure generally relates to compositions and methods for supporting skin barrier health. More particularly, the disclosure is directed to the use of a composition comprised of a combination of specific active ingredient blends which, when applied onto skin, help to support skin barrier homeostasis by downregulating the body's pro-inflammatory response to free radical-induced oxidative stress, inhibiting trans-epidermal water loss, and managing keratinocyte hyper-proliferation to preserve skin barrier integrity.

BACKGROUND

Skin is subject to damage, and resultant inflammation, by a number of extrinsic (environmental), and intrinsic (biological) factors. Examples of extrinsic factors include exposure to ultraviolet (UV) rays emanating from the sun, as well as harmful chemical agents found in airborne pollution such as smog and cigarette smoke. Intrinsic factors that negatively impact skin include, for example, chronological aging, a person's genetic makeup, and other biological changes that occur from within the skin. These factors cause skin to experience deleterious cellular effects associated with oxidative stress caused by harmful free radicals in the skin.

The problem with free radicals is that they steal electrons from healthy cells in the skin, causing oxidative stress. This in turn activates enzymes in the skin that break down collagen and damage the DNA of a cell, resulting in sunburn and premature aging. Photoaging caused by UV exposure is characterized by wrinkling and yellowing of the skin, along with other physical changes such as cracking, telangiectasia (spider vessels), solar keratosis (growths), ecchymoses (subcutaneous hemorrhagic lesions), and loss of elasticity (sagging).

Regarding other environmental aging factors such as air pollution, chemicals present therein are either themselves free radicals or have the ability to drive free-radical formation. These free radicals, when present within a biological setting such as the skin, cause a flow of electrons from one molecule to another. The importance of this process lies in the reactivity of the molecules involved.

Under normal conditions, electrons orbit around atoms in pairs, having opposite spins. When an atom has a single unpaired electron, its reactivity increases markedly, at which point it is referred to as a free radical. In a biological setting, free radicals are potentially very dangerous because they can react indiscriminately with neighboring molecules such as proteins, DNA, and vital cell structures such as the cell membrane. This process of electron stealing leads to oxidation. If these reactions are numerous, they can cause extensive cellular damage. The extent of damage depends on the availability of neutralizing antioxidant cellular defenses, as these specialized molecules preferentially react with free radicals, thus neutralizing them.

These cellular defense mechanisms help to reduce the amount of damage that free radicals and reactive species of radicals may cause to the skin by scavenging free radicals or enzymatically converting the free radicals to less toxic chemical species, thereby serving a physiological role, similar to antioxidants. The body's antioxidant defense system can become impaired, however, by the aging process and/or compromised by, for example, inflammation/erythema, infection, and other disorders characterized by oxidative stress.

Oxidative stress has also been found to negatively impact water homeostasis of the skin, i.e., the ability of the skin to maintain adequate hydration levels. It is important to the health and appearance of skin to keep it nourished to help counteract the damage caused by oxidative stress. Dry skin is a particularly common disorder that affects both males and females equally and is particularly prevalent in older individuals and those genetically predisposed to such a condition. People suffering from dry skin complain of flaking, itching, irritation, and an overall dull, rough, and lackluster appearance to their skin.

Moreover, as a person ages, their skin tends to produce fewer natural oils that aid in preventing moisture from escaping from, and thus dehydrating, the skin. Disruption of water homeostasis occurs at an early stage as a person's skin ages. This is because the expression of aquaporin-3, one of the proteins that regulates water flow at a cellular level, decreases as a person ages. Skin lacking in hydration cannot rid itself of toxins, resulting in irritation and inflammation. Thus, by maintaining good hydration of the surface layers of the skin, epidermis, and horny layer in particular, it becomes possible to substantially enhance the effectiveness of endogenous antioxidant molecules as discussed below, as well as cosmetic agents exhibiting antioxidant properties, to help alleviate oxidative stress. Properly hydrated skin slows the aging process by helping to maintain skin's elasticity.

The skin itself has a strong antioxidant defense mechanism to prevent and protect against UV-induced oxidative stress. This is accomplished via endogenous antioxidants such as superoxide dismutase (SOD), catalase, and other molecules like glutathione (GSH) that reduce the formation of ROS prior to the occurrence of oxidative changes in the tissue. The combination of SOD and catalase completely scavenges superoxide ion-initiating ROS. Unfortunately, prolonged UV exposure prevents cutaneous antioxidants such as SOD, catalase, and others from continuously performing these functions, thereby inevitably resulting in oxidative damage to the tissue and unmitigated ROS formation. Eventually, serious skin disorders such as photoaging and skin cancer can be realized.

Another important defense against oxidative stress is skin's barrier function. The term "barrier function" refers to the outermost layer of the skin, the stratum corneum, a.k.a. "the skin barrier", which is responsible for keeping moisture in, while keeping damaging elements like UV rays and free radicals out. When the skin's barrier function is operating properly, skin is firm, plump, and hydrated. However, when the barrier function deteriorates, skin health deteriorates as well.

The stratum corneum is the primary line of defense between an individual and the outside world, preventing environmental chemicals and biological irritants from penetrating the skin. For example, free radicals, bacteria, other microbes, allergens, toxic chemicals, UV light, and the like are blocked by the stratum corneum from penetrating into the skin. This is typically referred to as the stratum corneum's "physical" defense mechanism.

While protection against external assaults is a very important function served by the stratum corneum, an even more important function is to prevent the escape of water. The stratum corneum is made up of multiple stacks of flattened cells or "corneocytes," each of which is encased in a thick coating of fat, a.k.a., lipids. If one were to compare the stratum corneum to a brick wall, the stack of cells are bricks, and the fatty matrix encasing them is the mortar. Together, they form a barrier that keeps skin's water content inside so that the skin stays firm, hydrated, elastic, and less prone to wrinkling.

The lipid portion of the stratum corneum is what primarily provides it with its water-sealing properties. The lipids of the stratum corneum are comprised of various oily compounds naturally produced by the human body. These oily compounds include di-, and triglycerides, fatty acids, ceramides, cholesterol, and squalene. These lipids form a kind of multi-layered matrix that surrounds the skin cells. This matrix is semi-permeable, waterproofing and provides structure to the skin barrier by holding the skin cells tightly in place.

The stratum corneum is oftentimes damaged by various extrinsic (environmental), and intrinsic (biological) factors. Examples of extrinsic factors include exposure to UV rays and harmful chemical agents found in airborne pollutants like car exhaust, smog and cigarette smoke. Intrinsic factors that negatively impact skin include, for example, chronological aging, a person's genetic makeup, and other biological changes that occur within the skin and body. These factors have deleterious cellular effects on the stratum corneum due to oxidative stress caused by harmful free radicals.

While the damage caused by UV rays in terms of sunburn, photoaging and skin cancer have been extensively studied, UVB rays have also been found to cause damage to the stratum corneum whose protective wall is comprised of corneocytes (bricks) and lipids (oily mortar) begins to deteriorate upon exposure. This is believed to be caused by delamination of the stratum corneum's lipid matrix resulting in a decrease in intercellular strength, strain, and cohesion between the corneocytes and lipids. UV exposure naturally dries out the skin. Once the skin becomes dry and flaky, the ability of the corneocytes and lipids to form a strong, cohesive matrix is compromised leading to cracks and gaps being formed within the stratum corneum which provide a pathway for pathogens to enter and water to escape.

The negative impact of free radicals on the stratum corneum is also highly problematic as previously discussed. These free radicals, when present within a biological setting such as the stratum corneum, cause a flow of electrons from one molecule to another resulting in cellular damage and degradation of the stratum corneum in the process. The extent of damage depends on the availability of neutralizing antioxidant cellular defenses produced by the body.

Because oxidative stress negatively impacts the ability of the skin to maintain constant hydration levels, it is important to the health and appearance of skin to keep it properly hydrated. Aside from drinking plenty of water, maintaining proper hydration levels is highly dependent on a properly functioning stratum corneum. A compromised stratum corneum, unable to effectively seal water within the skin, causes skin to become dry. People suffering from dry skin complain of flaking, itching, irritation, and an overall dull, rough, and lackluster appearance to their skin. Hence, while protection against external physical assaults is an important function served by the stratum corneum, an equally important function is to prevent dry skin-inducing water loss.

Despite its importance, the barrier formed by the stratum corneum is quite delicate and prone to thinning as a person ages. Moreover, any assault on the stratum corneum, either from external physical assaults or cellular water loss, can lead to sensitized, dehydrated skin that is susceptible to environmental harm, dryness, irritation, breakout, sagging, and other signs of aging. When skin is dry, it is more permeable to irritants and allergens that can trigger inflammation that in turn can cause rosacea, acne, eczema, and premature aging.

The most common cosmetic approach to dealing with free radicals present in the skin and the damage they cause to the stratum corneum via oxidative stress involves the use of antioxidants which, when applied onto the skin, seek out and neutralize any free radicals they encounter. The goal of antioxidant-containing products is to neutralize free radicals present in the skin to mitigate the damage they can do to the skin cells that make up the stratum corneum. This is a very common solution for both reactively and proactively supporting the stratum corneum and there is no shortage of cosmetic products on the market today that employ this solution for skin barrier repair and maintenance. There continues to be, however, a need for ancillary solutions for dealing with skin cell-damaging oxidative stress.

Inflammation is the body's physiological response to, among other things, damage to skin cells caused by free radical-induced oxidative stress. It is a complex cascade of immune mechanisms meant to overcome tissue injury and initiate the healing process by recruiting various immune cells, chemical mediators such as vasoactive peptides and amines, pro-inflammatory cytokines, eicosanoids, and acute-phase proteins to prevent tissue damage and ultimately complete restoration of tissue function. This physiological phenomenon is commonly referred to as the inflammatory cascade. This phenomenon, while obviously important to the protection and restoration of tissue damaged by free radical-induced oxidative stress, it can also cause harmful damage to adjacent tissue cells and non-tissue cell components that are not experiencing, and being damaged by, oxidative stress. A useful analogy might be that of radiation chemotherapy used to treat cancer. While this chemotherapy treatment is meant to eliminate cancerous cells present in the body, it unfortunately oftentimes also eliminates healthy cells in the process. In short, the inflammatory cascade is a kind of double-edged sword that can simultaneously help restore skin cells damaged by free radical-induced oxidative stress, while damaging healthy cells. The ability to down-regulate the body's pro-inflammatory cellular signaling response to oxidative stress represents the best of both worlds.

Keratinocytes form the skin barrier by undergoing a highly complex differentiation process that involves changing their morphology and structural integrity, a process referred to as cornification. Alterations in the epidermal cornification process, such as occurs in the event of keratinocyte hyperproliferation involving uncontrolled keratinocytes formation negatively affects the formation of the skin barrier. Typically, this results in a disturbed barrier, which allows the entry of substances into the skin that are immunologically reactive. This contributes to, and promotes, inflammatory processes in the skin. In many common skin diseases, including atopic dermatitis and psoriasis, a defect in the formation of the skin barrier is observed.

Based on the foregoing, it is an object of embodiments of the present disclosure to provide skin care compositions and methods that positively influence the body's inflammatory cascade in response to oxidative stress in a way that mitigates the damage experienced by adjacent healthy skin cells.

It is also an object of embodiments of the present disclosure to provide skin care compositions and methods that help to support skin barrier hydration, integrity, and functionality.

It is also an object of the present disclosure to provide skincare compositions and methods that help mitigate skin barrier-disrupting keratinocyte hyperproliferation, thereby helping the skin barrier remain in functional homeostasis.

SUMMARY

The present disclosure is directed to a composition intended for application onto human skin comprising a mixture of: (1) a first active blend of at least: (a) Jojoba oil/Macadamia seed oil esters; (b) squalene; (c) phytosteryl macadamiate; and (d) phytosterols; (2) a second active blend of at least: (e) EGF growth factor; (f) IGF-1 growth factor; (g) acidic FGF growth factor; (h) basic FGF growth factor; (i) VEGF growth factor; (j) vitamin B9; and (k) acetyl glutamine; and (3) a third active blend of at least: (l) an extract of lithothamnium calcareum; (m) pentylene glycol; (n) lactic acid; and (o) glycerin; and (4) a dermatologically acceptable carrier, wherein (1)-(3) are employed in amounts sufficient to down-regulate pro-inflammatory cellular signaling, promote water retention, and mitigate keratinocyte hyperproliferation in skin to help support skin barrier homeostasis.

The present disclosure is also directed to a method of supporting skin barrier homeostasis by applying the above-disclosed composition onto human skin.

According to another embodiment, the present disclosure is also directed to a method of downregulating pro-inflammatory cellular signaling, promoting water retention, and mitigating keratinocyte hyperproliferation in skin by applying the above-disclosed composition onto human skin.

These and other features, aspects and advantages of the present disclosure will become evident to those skilled in the art from a reading of the present disclosure.

DETAILED DESCRIPTION

The compositions of the present disclosure can comprise, consist essentially of, or consist of, the components of the present disclosure as well as other ingredients described herein. The term "comprising" as used herein is meant to include various optional, compatible components that can be used in the preservative systems and cosmetic compositions of the present disclosure without limiting the inclusion, use of, or cooperation with other ingredients, excipients, uses, or otherwise. The term "consisting essentially of" as used herein means that the composition or component may include additional ingredients, but only if the additional ingredients do not materially alter the basic and novel characteristics of the compositions or methods.

As used herein, the words "preferred," "preferably," and variants thereof refer to embodiments of the disclosure that afford certain benefits under certain circumstances. However, other embodiments may also be preferred under the same or other circumstances. Furthermore, the recitation of one or more preferred embodiments does not imply that other embodiments are not useful and is not intended to exclude other embodiments from the scope of the disclosure.

Numerical ranges as used herein are intended to include every number and subset of numbers contained within that range, whether specifically disclosed or not. Further, these numerical ranges should be construed as providing support for a claim directed to any number or subset of numbers within that range.

All percentages, parts, proportions, and ratios as used herein are by weight of the total composition, unless otherwise specified. All such weights as they pertain to listed ingredients are based on the active level.

All references to singular characteristics or limitations of the present disclosure shall include the corresponding plural characteristic or limitation, and vice versa, unless otherwise specified or clearly implied to the contrary by the context in which the reference is made.

All publications, articles, papers, patents, patent publications, and other references cited herein are hereby incorporated in their entireties for all purposes to the extent consistent with the disclosure herein.

The term "dry skin-inducing water loss" as described herein refers to an amount of trans-epidermal water loss (TEWL) that causes skin to become dry, flaky, itchy and irritated, all signs of an improperly functioning stratum corneum/skin barrier.

The term "oxidative stress" as described herein refers to the disturbance in balance between reactive oxygen species (ROS), reactive nitrogen species (RNS) and/or other free radicals and antioxidants present in the skin caused by extrinsic and/or intrinsic factors. Extrinsic factors include, for example, exposure to UV radiation, pollution, and products containing harsh chemicals. Intrinsic factors include, for example, chronological aging, a person's genetic makeup, and other biological changes that occur from within the skin.

The term "free radicals" as described herein refers to those ROS and/or RNS that are formed when skin experiences oxidative stress caused by extrinsic and/or intrinsic factors.

The term "keratinocyte hyperproliferation" as described herein refers to uncontrolled epidermal cellular differentiation in support of skin barrier integrity.

The term "skin barrier homeostasis" as described herein refers to the ability of the stratum corneum to maintain balanced hydration levels in support of skin barrier integrity and functionality.

The present disclosure generally relates to compositions and methods for positively influencing (1) pro-inflammatory cellular signaling in response to oxidative stress, (2) hydration levels within the skin barrier, and (3) keratinocyte hyperproliferation in order to help support skin barrier homeostasis.

It has surprisingly been discovered by the inventors that a composition comprising a mixture of: (1) a first active blend of at least: (a) Jojoba oil/Macadamia seed oil esters; (b) squalene; (c) phytosteryl macadamiate; and (d) phytosterols; (2) a second active blend of at least: (e) EGF growth factor; (f) IGF-1 growth factor; (g) acidic FGF growth factor; (h) basic FGF growth factor; (i) VEGF growth factor; (j) vitamin B9; and (k) acetyl glutamine; and (3) a third active blend of at least: (l) an extract of lithothamnium calcareum; (m) pentylene glycol; (n) lactic acid; and (o) glycerin; (4) an emulsifier; and (5) a dermatologically acceptable carrier, when applied onto skin, downregulates pro-inflammatory cellular signaling in oxidatively-stressed skin, promotes water retention, and mitigates keratinocyte hyperproliferation to help support skin barrier homeostasis.

A first active blend comprised of: (a) Jojoba oil/Macadamia seed oil esters; (b) squalene; (c) Phytosteryl Macadamiate; and (d) phytosterols, is one of the three key constituents of the composition of the present disclosure. The active blend represents a lipid complex meant to mimic the surface lipid profile of a healthy, young adult and is used to help balance the stratum corneum's lipid network.

This first active blend is commercially available from International Flora Technologies, Ltd under the tradename L22®.

The first active blend may be employed in an amount of from about 0.25% to about 6% by weight, preferably in an amount of from about 0.25% to about 5% by weight, and more preferably in an amount of from about 0.25% to about 4% by weight, all weights based on the total weight of the composition.

A second active blend comprised of: (e) EGF growth factor; (f) IGF-1 growth factor; (g) acidic FGF growth factor; (h) basic FGF growth factor; (i) VEGF growth factor; (j) vitamin B9; and (k) acetyl glutamine, is another of the three key constituents of the composition. The active blend represents a combination of specific types of growth factors, amino acids and vitamins used for its efficacy in diminishing the appearance of wrinkles in human skin and other anti-aging benefits.

This second active blend is commercially available from Labio. Co., Ltd under the tradename BIO-PLACENTA®.

The second active blend may be employed in an amount of from about 0.1 to about 6% by weight, preferably in an amount of from about 0.1% to about 5% by weight, and more preferably in an amount of from about 0.25% to about 4% by weight, all weights based on the total weight of the composition.

A third active blend comprised of: (l) an extract of lithothamnium calcareum; (m) pentylene glycol; (n) lactic acid; and (o) glycerin, is the last of the three key constituents of the composition. The active blend represents a mixture of natural moisturizers used as a skin barrier enhancer due to its ability to provide hydration to the skin and defend against TEWL.

This third active blend is commercially available from Provital, S.A.U. under the tradename HYDRAFENCE™.

The third active blend may be employed in an amount of from about 0.25 to about 6% by weight, preferably in an amount of from about 0.25 to about 5% by weight, and more preferably in an amount of from about 0.25 to about 4% by weight, all weights based on the total weight of the composition.

According to one embodiment of the present disclosure, there is provided a composition intended for application onto human skin to help support skin barrier homeostasis, the composition comprising a mixture of: (1) a first active blend of at least: (a) Jojoba oil/Macadamia seed oil esters; (b) squalene; (c) phytosteryl macadamiate; and (d) phytosterols; (2) a second active blend of at least: (e) EGF growth factor; (f) IGF-1 growth factor; (g) acidic FGF growth factor; (h) basic FGF growth factor; (i) VEGF growth factor; (j) vitamin B9; and (k) acetyl glutamine; and (3) a third active blend of at least: (l) an extract of lithothamnium calcareum; (m) pentylene glycol; (n) lactic acid; and (o) glycerin; (4) an emulsifier; and (5) a dermatologically acceptable carrier, wherein (1)-(3) are employed in amounts sufficient to downregulate pro-inflammatory cellular signaling in oxidatively-stressed skin, thereby helping to support skin barrier homeostasis.

The inventors have surprisingly and unexpectedly discovered that a mixture of the three above-disclosed active blends, when applied onto skin, synergistically: (1) downregulates the inflammatory cascade triggered by oxidative stress in the stratum corneum, thereby mitigating damage experienced by healthy skin cells; (2) positively influences skin barrier-disrupting keratinocyte hyperproliferation; and (3) helps promote water retention by the skin, thereby helping to maintain skin barrier homeostasis. These synergies are only realized in the presence of the mixture. None of the three active blends, individually, yielded these synergistic skin barrier benefits.

The dermatologically acceptable carrier can encompass a wide variety of forms. In some cases, the solubility or dispersibility of the components in the composition may dictate the form and character of the carrier. Non-limiting examples include simple solutions (e.g., aqueous or anhydrous), dispersions, emulsions, and solid forms. In certain embodiments, the dermatologically acceptable carrier is in the form of an emulsion. An emulsion can be generally classified as having a continuous aqueous phase (e.g., oil-in-water and water-in-oil-in-water) or a continuous oil phase (e.g., water-in-oil or oil-in-water).

Any ingredient capable of emulsifying the composition may be employed as an emulsifier without departing from the spirit of the disclosure, so long as it is dermatologically acceptable. Examples thereof include, but are not limited to, glyceryl stearate, cetyl alcohol, sodium stearoyl lactylate, sorbitan olivate, cetearyl olivate, cetearyl alcohol, cetearyl glucoside, sodium cetearyl sulfate, and the like. It is also particularly preferred that the emulsifier be free of palm oil.

The compositions of the present disclosure may be made available to consumers in a wide variety of product forms that include, but are not limited to, solutions, suspensions, lotions, creams, gels, sprays, ointments, foams, and serums.

According to embodiments of the present disclosure, the compositions can also additionally comprise suitable optional ingredients as desired. For example, the composition can optionally include other active and/or inactive ingredients, provided they do not unacceptably alter the synergistic benefits of the skin care composition. The selection and precise amount of optional ingredients will be determined by those skilled in the art.

In yet another embodiment of the present disclosure, there is provided a method of downregulating pro-inflammatory cellular signaling in oxidatively stressed skin by applying one of the above-disclosed compositions onto the skin.

A further embodiment of the present disclosure provides for a method of positively influencing skin hydration to help support skin barrier homeostasis by applying one of the above-disclosed compositions onto oxidatively stressed skin.

In yet another embodiment of the present disclosure, there is provided a method of mitigating skin barrier-disrupting keratinocyte hyper-proliferation to support skin barrier integrity and functionality.

EXAMPLES

The following examples as set forth herein are intended for illustrative purposes only and are not intended to limit the scope of the disclosure in any way, as many variations thereof are possible without departing from the spirit and scope of the disclosure. In the examples, all concentrations are listed as weight percent, unless otherwise specified.

Example 1

Gene expression testing was performed in order to ascertain whether the composition of the present disclosure exhibited any synergistic properties as compared to its three key constituents, individually. Briefly, Reconstructed Human Epidermis (RHE) tissues were incubated with: (i) the first active blend of Jojoba oil/Macadamia seed oil esters+squalene+phytosteryl macadamiate+phytosterols; (ii) the second active blend of EGF growth factor+IGF-1 growth factor+acidic FGF growth factor+basic FGF growth factor+ VEGF growth factor+vitamin B9+acetyl glutamine; (iii) the third active blend of an extract of lithothamnium calcareum+ pentylene glycol+lactic acid+glycerin; and (iv) a combination of (i)-(iii). Following the incubation, RNA was extracted from the tissue, and real time quantitative PCR was performed. The efficiency ΔΔCt method was used for quantification of results, after the normalization of gene expression to conventional housekeeping genes. Genes were considered differentially expressed if there was a ±1.5 average Fold Change that was statistically significant. Statistical significance was based on the p value being ≤0.05.

While tissue treated with each of the individual active blends showed bioactivity, it was surprisingly discovered that tissues treated with a composition containing all three active blends exhibited "synergistic" bioactivity in its ability to down-regulate pro-inflammatory cellular signaling, support skin barrier homeostasis, and positively influence keratinocyte proliferation, as is seen in Table 1, below.

TABLE 1

| Ingredient | Amount (wt %) | Avg Fold Change for CX3CR1 | P-val for CX3CR1 | Avg Fold Change for DDX58 | P-val for DDX58 | Avg Fold Change for CDK4 | P-val for CDK4 | Avg Fold Change for SHROOM3 | P-val for SHROOM3 |
|---|---|---|---|---|---|---|---|---|---|
| First active blend | 3.0% | 1.00 | 0.55 | −1.17 | 0.66 | −1.33 | 0.35 | 1.05 | 0.76 |
| Second active blend | 0.5% | −1.06 | 0.99 | 1.06 | 0.87 | 1.04 | 0.55 | −1.71 | 0.12 |
| Third active blend | 0.25% | −1.52 | 1.2 | −1.61 | 0.25 | −1.28 | 0.31 | −1.20 | 0.36 |
| Complex 1 | 3.75% | −2.12 | 0.04 | −2.02 | 0.04 | −1.91 | 0.03 | −2.03 | 0.03 |

| Ingredient | Amount (wt %) | Avg Fold Change for TAF15 | P-val for TAF15 | Avg Fold Change for LRRC8A | P-val for LRRC8A | Avg Fold Change for CLCN6 | P-val for CLCN6 | Avg Fold Change for IFI16 | P-val for IFI16 |
|---|---|---|---|---|---|---|---|---|---|
| First blend | 3.0% | −1.29 | 0.52 | 1.49 | 0.056 | 1.07 | 0.89 | −1.50 | 0.06 |
| Second blend | 0.5% | 1.09 | 0.38 | −1.56 | 0.008 | −1.03 | 0.09 | 1.27 | 0.12 |
| Third blend | 0.25% | −1.09 | 0.64 | 1.53 | 0.006 | 1.01 | 0.96 | −1.55 | 0.10 |
| Complex 1 | 3.75% | −1.73 | 0.01 | 1.71 | 0.002 | −1.77 | 0.001 | −1.98 | 0.003 |

The data in Table 1 shows that tissue treated with the composition of the present disclosure induced a statistically significant synergistic down-regulation of pro-inflammatory cell signaling. More particularly, with regards to genes CX3CR1, DDX58, and SHROOM3, only the mixture exhibited statistically significant (i.e., P-val≤0.05) and synergistic (i.e., Avg Fold Change of greater than or equal to ±1.5) differential expression of these genes, as compared to each individual active blend.

In addition, it was also surprisingly discovered that genes TAF15, LRRC8A, CLDN-6, CDK4, and IFI16 also showed statistically significant synergistic differential expression only in the presence of the composition and not in the presence of the individual blends. Genes TAF15, CLDN-6, and CDK4 covering keratinocyte hyperproliferation and LRRC8A covering cellular osmotic (water retention) changes, by virtue of their being synergistically expressed by the inventive mixture, evidence the ability of the mixture to synergistically enhance homeostasis within the skin. In addition, gene IFI16 (linked to inflammatory cytokine expression in cells) was also positively influenced to a statistically significant degree by the mixture, evidencing a synergistic improvement in skin barrier integrity and protective functionality.

Example 2

A second composition, also in accordance with the present disclosure, was evaluated for the presence of synergistic skin barrier-supporting properties.

TABLE 2

| Ingredient | Amount (wt %) | Avg Fold Change for IFI 16 | P-val for IFI 16 | Avg Fold Change for CDK4 | P-val for CDK4 | Avg Fold Change for LOX | P-val for LOX | Avg Fold Change for IL37 | P-val for IL37 |
|---|---|---|---|---|---|---|---|---|---|
| First active blend | 0.25% | 1.32 | 0.18 | 1.02 | 0.40 | 1.12 | 0.45 | 1.74 | 0.23 |
| Second active blend | 0.1% | −1.04 | 0.88 | −1.22 | 0.17 | −1.03 | 0.80 | 1.29 | 0.52 |
| Third active blend | 0.25% | −1.55 | 0.10 | 1.28 | 0.31 | −1.30 | 0.11 | 2.44 | 0.02 |
| Complex 2 | 0.6% | −1.55 | 0.10 | 1.05 | 0.60 | −1.68 | 0.005 | 1.97 | 0.02 |

Gene CDK4 relating to epidermal cellular differentiation evidences the ability of the composition to synergistically help support skin barrier integrity by positively influencing keratinocyte hyperproliferation. In addition, the genes LOX, IL37, and IFI16 relating to inflammatory cytokine expression in cells were also positively influenced to a statistically significant degree by the mixture, evidencing a synergistic improvement in managing the inflammatory cascade leading to enhanced skin barrier integrity and functionality.

Example 3

A skincare composition in accordance with the present disclosure was prepared comprising the ingredients shown in Table 3, below:

TABLE 3

| Ingredient (by tradename) | Wt. % |
|---|---|
| Bio-Placenta | 1.00% |
| Hydrafence | 0.25% |
| L22 | 3.00% |
| Carrier Vehicle | q.s. 100% |

The composition of Example 3 was clinically tested to evaluate its ability to help skin maintain water homeostasis (i.e., constant hydration levels) to help maintain skin barrier integrity. Thirty-two females aged 41-73 were asked to apply the composition under normal use conditions onto an area of skin surrounding their eye orbital twice a day, once in the morning and once at night. After taking an initial baseline reading, skin health and appearance data were collected 1 hour after initial application on day 0, then on day 7, and day 14.

Hydration data was collected using a Corneometer® which measures skin capacitance based on humidity levels in the skin. The results obtained are seen in Table 4, below.

TABLE 4

| Visit | Mean % improvement | % of subjects improved |
|---|---|---|
| Hour 1 (±10 minutes) | 18.0% | 96.9% |
| Day 7 | 4.6% | 56.3% |
| Day 28 | 25.8% | 90.6% |

The results obtained in Table 4 evidence the ability of the composition of Example 3 to support skin barrier integrity via significantly improved water homeostasis within the skin. Approximately 97% of test subjects experienced an 18.0% improvement in hydration after 1 hour post application, with approximately 91% of test subjects experiencing a 25.8% improvement after week 4.

Next, the composition of Example 3 was evaluated using Expert Clinical Grading Scores calculated using the Wilcoxon signed rank test with a null hypothesis that mean change from baseline is zero, to evaluate its effect on skin homeostasis, as is seen in Table 5, below.

TABLE 5

| Parameter | Visit | Mean % improvement | % of subject improved |
|---|---|---|---|
| Under Eye Dark Circles | Hour 1 (±10 mins) | 4.3 | 12.5 |
| | Day 7 | 14.9 | 62.5 |
| | Day 28 | 21.3 | 75.0 |
| Fine Lines in Crows Feet Area | Hour 1 (±10 mins) | 2.1 | 6.3 |
| | Day 7 | 14.9 | 62.5 |
| | Day 28 | 21.3 | 71.9 |
| Wrinkles in Crows Feet Area | Hour 1 (±10 mins) | 0.0 | 0.0 |
| | Day 7 | 6.5 | 18.8 |
| | Day 28 | 15.2 | 56.3 |
| Radiance of Skin in Eye Area treated | Hour 1 (±10 mins) | 14.8 | 53.1 |
| | Day 7 | 24.1 | 68.8 |
| | Day 28 | 31.5 | 87.5 |
| Under Eye Puffiness | Hour 1 (±10 mins) | 5.9 | 28.1 |
| | Day 7 | 15.7 | 79.1 |
| | Day 28 | 31.4 | 96.9 |
| Sagging in Eye Area | Hour 1 (±10 mins) | 2.5 | 6.3 |
| | Day 7 | 7.5 | 25.0 |
| | Day 28 | 20.0 | 59.4 |

Expert Clinical Grading data showed that the composition of Example 3 significantly improved the parameters identified in Table 6 after weeks 1 and 4 evidencing the ability of the inventive composition to help support skin barrier integrity and homeostasis.

The test subjects were then asked to assess, qualitatively, their impression of the composition's efficacy on their skin. 10 out of 15 had a positive impression after the initial application; 15 out of 15 had a positive impression after 7 days; and 15 out of 15 had a positive impression after 14 days of use.

Example 4

A skincare composition in accordance with the present disclosure was prepared comprising the ingredients shown in Table 6:

TABLE 6

| Ingredient (by tradename) | Wt. % |
|---|---|
| Bio-Placenta | 0.10% |
| Hydrafence | 0.25% |

TABLE 6-continued

| Ingredient (by tradename) | Wt. % |
| --- | --- |
| L22 | 0.25% |
| Carrier Vehicle | q.s. 100% |

The composition of Example 4 was clinically tested to evaluate its ability to address skin barrier-disrupting keratinocyte hyperproliferation in the form of keratosis pilaris. Twenty-one individuals aged 18-61 were asked to apply the composition, twice a day, onto an area of their skin where the condition keratosis pilaris was present. After taking an initial baseline reading, data was collected 15 minutes (+5 mins) after initial application on day 0, then on day 7, and day 14.

Next, the composition of Example 4 was evaluated using Expert Clinical Grading Scores calculated using the Wilcoxon signed rank test with a null hypothesis that mean change from baseline is zero, to evaluate its effect on keratinocyte hyperproliferation, as is seen in Table 7, below.

TABLE 7

| Parameter | Visit | Mean % improvement | % of subject improved |
| --- | --- | --- | --- |
| Keratosis Pilaris | 15 mins (±5 mins) | 0.0 | 0.0 |
| | Day 7 (±1 day) | 0.0 | 4.8 |
| | Day 14 (±1 day) | 8.6 | 28.6 |
| Skin Texture | 15 mins (±5 mins) | 5.0 | 19.0 |
| | Day 7 (±1 day) | 17.5 | 61.9 |
| | Day 14 (±1 day) | 25.0 | 76.2 |
| Skin Flaking | 15 mins (±5 mins) | 68.8 | 81.0 |
| | Day 7 (±1 day) | 87.5 | 85.7 |
| | Day 14 (±1 day) | 87.5 | 85.7 |

Expert Clinical Grading data showed that the composition of Example 3 significantly improved all of the parameters identified in Table 8 after day 7 (+1 day) and day 14 (+1 day), evidencing the ability of the inventive composition to positively influence keratinocyte hyperproliferation and thereby support skin barrier integrity.

The test subjects were then asked to assess, qualitatively, their impression of the composition's efficacy on their skin. 9 out of 15 had a positive impression after the initial application; 12 out of 15 had a positive impression after 7 days; and 13 out of 15 had a positive impression after 14 days of use.

Example 5

A skincare composition in accordance with the present disclosure was prepared comprising the ingredients shown in Table 8, below:

TABLE 8

| Ingredient (by tradename) | Wt. % |
| --- | --- |
| Bio-Placenta | 3.00% |
| Hydrafence | 3.00% |
| L22 | 3.00% |
| Carrier Vehicle | q.s. 100% |

The composition of Example 5 was clinically tested to evaluate its ability to positively influence the appearance of fine lines, wrinkles, skin elasticity, and skin plumpness. Thirty-three females aged 35-70 were asked to apply the composition under normal use conditions onto their face twice a day, once in the morning and once at night. After taking an initial baseline reading, skin health and appearance data were collected 15 minutes after initial application on day 0, then on day 7, and finally on day 28.

Hydration data was collected using a CORNEOMETER® which measures skin capacitance based on humidity levels in the skin. The results obtained are seen in Table 9, below.

TABLE 9

| Visit | Mean % improvement | % of subjects improved |
| --- | --- | --- |
| 15 minutes | 32.0% | 93.9% |
| Day 7 | −13.8% | 45.5% |
| Day 28 | 15.1% | 75.8% |

The results obtained in Table 9 evidence the ability of the composition of Example 5 to support skin barrier integrity via significantly improved water homeostasis within the skin. Approximately 94% of test subjects experienced an 32.0% improvement in hydration after 15 minutes post application, with approximately 76% of test subjects experiencing a 15.1% improvement at day 28.

Next, the composition of Example 5 was evaluated using Expert Clinical Grading Scores calculated using the Wilcoxon signed rank test with a null hypothesis that mean change from baseline is zero, to evaluate its effect on skin homeostasis, as is seen in Table 10, below.

TABLE 10

| Parameter | Visit | Mean % improvement | % of subject improved |
| --- | --- | --- | --- |
| Skin Plumpness | 15 min. | Not Stat. Significant | N/A |
| | Day 7 | −6.0 | 53.3 |
| | Day 28 | −8.5 | 70.0 |
| Fine Lines | 15 min. | −6.7 | 63.3 |
| | Day 7 | −11.6 | 86.7 |
| | Day 28 | −15.8 | 86.7 |
| Wrinkles | 15 min. | N/A | N/A |
| | Day 7 | N/A | N/A |
| | Day 28 | −5.9 | 43.3 |
| Skin Firmness | 15 min. | N/A | N/A |
| | Day 7 | N/A | N/A |
| | Day 28 | −2.7 | 26.7 |
| Skin Elasticity | 15 min. | N/A | N/A |
| | Day 7 | N/A | N/A |
| | Day 28 | −2.4 | 23.3 |
| Overall Appearance of Skin (Healthy) | 15 min. | N/A | N/A |
| | Day 7 | N/A | N/A |
| | Day 28 | −5.6 | 60.0 |

Expert Clinical Grading data showed that the composition of Example 5 improved, in a statistically significant way, the parameters identified in Table 10 after evidencing the ability of the inventive composition to help support skin barrier integrity and homeostasis.

The test subjects were then asked to assess, qualitatively, their impression of the composition's efficacy on their skin in terms of its appearance and overall health. 93.9% had a positive impression 15 minutes after the initial application; and 90.9 had a positive impression after 7 and 28 days of use.

Example 6

A skincare composition in accordance with the present disclosure was prepared comprising the ingredients shown in Table 11, below:

TABLE 11

| Ingredient (by tradename) | Wt. % |
|---|---|
| Bio-Placenta | 4.00% |
| Hydrafence | 4.00% |
| L22 | 4.00% |
| Carrier Vehicle | q.s. 100% |

The composition of Example 6 was clinically tested to evaluate its ability to positively influence skin hydration levels and trans-epidermal water loss (TEWL). Thirty-one females aged 21-64 were asked to apply the composition under normal use conditions onto their face twice a day, once in the morning and once at night. After taking an initial baseline reading, skin health and appearance data were collected 30 minutes (+/−5 min.) after initial application on day 0 and on day 14.

Hydration data was collected using a CORNEOMETER® which measures skin capacitance based on humidity levels in the skin. The results obtained are seen in Table 12 below.

TABLE 12

| Visit | Mean % improvement | % of subjects improved |
|---|---|---|
| 30 minutes (+/− 5 min.) | 22.7% | 93.5% |
| Day 14 | 21.7% | 83.9% |

The results obtained in Table 12 evidence the ability of the composition of Example 6 to support skin barrier integrity as is evidenced by the significant improvement in hydration levels within the skin. Approximately 94% of test subjects experienced a 22.7% improvement in hydration after 30 minutes post application, with approximately 84% of test subjects experiencing a 21.7% improvement at day 14.

Trans-epidermal water loss (TEWL) data was collected using a VAPOMETER® which measures relative humidity levels in the skin. The results obtained are seen in Table 13, below.

TABLE 13

| Visit | Mean % improvement | % of subjects improved |
|---|---|---|
| 30 minutes (+/− 5 min.) | 13.9% | 93.5% |
| Day 14 | 17.9% | 90.3% |

The results obtained in Table 13 evidence the ability of the composition of Example 5 to support skin barrier integrity as is evidenced by reduced TEWL by the skin evidencing an improvement in skin barrier function. Approximately 94% of test subjects experienced a 13.9% improvement in reduced TEWL after 30 minutes post application, with approximately 90% of test subjects experiencing a 17.9% improvement at day 14.

The test subjects were then asked to assess, qualitatively, their impression of the composition's efficacy on their skin in terms of its appearance and overall health. 100% had a positive impression of their skin 30 minutes after the initial application, and after 14 days of use.

By providing skin care compositions and methods according to the present disclosure, the damage done to healthy skin cells when the body responds to oxidative stress in the stratum corneum can be synergistically mitigated in a statistically significant way. The downregulation of pro-inflammatory cellular signaling in response to oxidative stress mitigates the damage done to healthy skin cells during the body's inflammatory response to oxidative stress.

In addition, the findings relating to both keratinocyte proliferation (epidermal cellular differentiation) and water homeostasis (cellular osmotic changes) validate the invention's ability to synergistically support skin barrier homeostasis/equilibrium and, consequently, skin barrier health and functionality.

The skilled artisan will recognize the interchangeability of various components of different embodiments described. Besides the variations described, other known equivalents for each feature can be mixed and matched by one of ordinary skill in this art to arrive at a preservative system under principles of the present disclosure. Therefore, the embodiments described may be adapted to preservative systems for other types of compositions and for other uses than those described and having other components than those described.

Although compositions and methods have been disclosed in certain preferred embodiments and examples, it nevertheless will be understood by those skilled in the art that the present disclosure extends beyond the disclosed embodiments to other alternative embodiments and/or uses of the disclosure and obvious modifications and equivalents. It is intended that the scope of the present disclosure should not be limited by the disclosed embodiments described above but should be determined only by a fair reading of the claims that follow.

What is claimed is:

1. A composition intended for application onto human skin experiencing oxidative stress, the composition comprising:
   (1) a first active blend in an amount from about 0.25% to about 6% by weight of at least:
   (a) Jojoba oil/Macadamia seed oil esters;
   (b) squalene;
   (c) phytosteryl macadamiate; and
   (d) phytosterols;
   (2) a second active blend in an amount of from about 0.1% to about 6% by weight of at least:
   (e) epidermal growth factor (EGF);
   (f) insulin-like growth factor-1 (IGF-1);
   (g) acidic fibroblast growth factor (aFGF);
   (h) basic fibroblast growth factor (bFGF);
   (i) vascular endothelial growth factor (VEGF);
   (j) vitamin B9; and
   (k) acetyl glutamine; and
   (3) a third active blend in an amount of about 0.25% to about 6% by weight of at least:
   (l) an extract of lithothamnium calcareum;
   (m) pentylene glycol;
   (n) lactic acid; and
   (o) glycerin;
   (4) an emulsifier; and
   (5) a dermatologically acceptable carrier,
   wherein (1)-(3) are employed in amounts sufficient to help support skin barrier health, integrity, and functionality, wherein all weights are based on the total weight of the composition.

2. The composition of claim 1, wherein (1) is employed in an amount of from about 0.25 to about 5% by weight; (2) is employed in an amount of from about 0.1 to about 5% by weight; and (3) is employed in an amount of from about 0.25 to about 5% by weight, all weights based on the total weight of the composition.

3. The composition of claim 1, wherein (1) is employed in an amount of from about 0.25 to about 4% by weight; (2) is employed in an amount of from about 0.25 to about 4% by weight; and (3) is employed in an amount of from about 0.25 to about 4% by weight, all weights based on the total weight of the composition.

4. A method of downregulating pro-inflammatory cellular signaling in oxidatively-stressed skin by applying onto the skin a composition comprising:
   (1) a first active blend in an amount from about 0.25% to about 6% by weight of at least:
   (a) Jojoba oil/Macadamia seed oil esters;
   (b) squalene;
   (c) phytosteryl macadamiate; and
   (d) phytosterols;
   (2) a second active blend in an amount of from about 0.1% to about 6% by weight of at least:
   (e) epidermal growth factor (EGF);
   (f) insulin-like growth factor-1 (IGF-1);
   (g) acidic fibroblast growth factor (aFGF);
   (h) basic fibroblast growth factor (bFGF);
   (i) vascular endothelial growth factor (VEGF);
   (j) vitamin B9; and
   (k) acetyl glutamine; and
   (3) a third active blend in an amount of about 0.25% to about 6% by weight of at least:
   (l) an extract of lithothamnium calcareum;
   (m) pentylene glycol;
   (n) lactic acid; and
   (o) glycerin;
   (4) an emulsifier; and
   (5) a dermatologically acceptable carrier,
   wherein (1)-(3) are employed in amounts sufficient to down-regulate pro-inflammatory cellular signaling in skin to help support skin barrier homeostasis, wherein all weights are based on the total weight of the composition.

5. The method of claim 4 wherein (1) is employed in an amount of from about 0.25 to about 5% by weight; (2) is employed in an amount of from about 0.1 to about 5% by weight; and (3) is employed in an amount of from about 0.25 to about 5% by weight, all weights based on the total weight of the composition.

6. The method of claim 4 wherein (1) is employed in an amount of from about 0.25 to about 4% by weight; (2) is employed in an amount of from about 0.25 to about 4% by weight; and (3) is employed in an amount of from about 0.25 to about 4% by weight, all weights based on the total weight of the composition.

7. A method of supporting skin barrier homeostasis by applying onto the skin a composition comprising: (1) a first active blend in an amount from about 0.25% to about 6% by weight of at least:
   (a) Jojoba oil/Macadamia seed oil esters;
   (b) squalene;
   (c) phytosteryl macadamiate; and
   (d) phytosterols;
   (2) a second active blend in an amount of from about 0.1% to about 6% by weight of at least:
   (e) epidermal growth factor (EGF);
   (f) insulin-like growth factor-1 (IGF-1);
   (g) acidic fibroblast growth factor (aFGF);
   (h) basic fibroblast growth factor (bFGF);
   (i) vascular endothelial growth factor (VEGF);
   (j) vitamin B9; and
   (k) acetyl glutamine; and
   (3) a third active blend in an amount of about 0.25% to about 6% by weight of at least:
   (l) an extract of lithothamnium calcareum;
   (m) pentylene glycol;
   (n) lactic acid; and
   (o) glycerin;
   (4) an emulsifier; and
   (5) a dermatologically acceptable carrier,
   wherein (1)-(3) are employed in amounts sufficient to positively influence hydration levels within skin to help support skin barrier homeostasis, wherein all weights are based on the total weight of the composition.

8. The method of claim 7 wherein (1) is employed in an amount of from about 0.25 to about 5% by weight; (2) is employed in an amount of from about 0.1 to about 5% by weight; and (3) is employed in an amount of from about 1 to about 5% by weight, all weights based on the total weight of the composition.

9. The method of claim 7 wherein (1) is employed in an amount of from about 1 to about 4% by weight; (2) is employed in an amount of from about 0.5 to about 4% by weight; and (3) is employed in an amount of from about 1 to about 4% by weight, all weights based on the total weight of the composition.

10. A method of mitigating skin barrier-disrupting keratinocyte hyperproliferation by applying onto the skin a composition comprising:
    (1) a first active blend in an amount from about 0.25% to about 6% by weight of at least:
    (a) Jojoba oil/Macadamia seed oil esters;
    (b) squalene;
    (c) phytosteryl macadamiate; and
    (d) phytosterols;
    (2) a second active blend in an amount of from about 0.1% to about 6% by weight of at least:
    (e) epidermal growth factor (EGF);
    (f) 0 insulin-like growth factor-1 (IGF-1);
    (g) acidic fibroblast growth factor (aFGF);
    (h) basic fibroblast growth factor (bFGF);
    (i) vascular endothelial growth factor (VEGF);
    (j) vitamin B9; and
    (k) acetyl glutamine; and
    (3) a third active blend in an amount of about 0.25% to about 6% by weight of at least:
    (l) an extract of lithothamnium calcareum;
    (m) pentylene glycol;
    (n) lactic acid; and
    (o) glycerin;
    (4) an emulsifier; and
    (5) a dermatologically acceptable carrier,
    wherein (1)-(3) are employed in amounts sufficient to positively influence keratinocyte hyperproliferation in skin to help support skin barrier homeostasis, wherein all weights are based on the total weight of the composition.

11. The method of claim 10 wherein (1) is employed in an amount of from about 0.25 to about 5% by weight; (2) is employed in an amount of from about 0.1 to about 5% by weight; and (3) is employed in an amount of from about 1 to about 5% by weight, all weights based on the total weight of the composition.

12. The method of claim 10 wherein (1) is employed in an amount of from about 1 to about 4% by weight; (2) is employed in an amount of from about 0.5 to about 4% by weight; and (3) is employed in an amount of from about 1 to about 4% by weight, all weights based on the total weight of the composition.

* * * * *